United States Patent [19]

Grace

[11] Patent Number: 5,340,571
[45] Date of Patent: Aug. 23, 1994

[54] NON-AEROSOL SHAVING GEL

[75] Inventor: William R. Grace, Reading, Mass.

[73] Assignee: The Gillette Company, Boston, Mass.

[21] Appl. No.: 37,958

[22] Filed: Mar. 26, 1993

[51] Int. Cl.⁵ ................................................ A61K 7/15
[52] U.S. Cl. ..................................... 424/73; 514/944
[58] Field of Search ......................................... 424/73

[56] References Cited

U.S. PATENT DOCUMENTS

| | | | |
|---|---|---|---|
| 3,541,581 | 11/1970 | Monson | 252/90 |
| 4,744,979 | 5/1988 | Osipow et al. | 424/73 |
| 4,957,732 | 9/1990 | Grollier et al. | 424/73 |
| 5,034,220 | 7/1991 | Helioff et al. | 424/73 |

FOREIGN PATENT DOCUMENTS 259843 3/1988 European Pat. Off. .
91/07943 6/1991 PCT Int'l Appl. .

OTHER PUBLICATIONS

Cosmetics and Toiletries 91:65–70 (1976).
Harry's Cosmeticology, 7th Ed. (1982) pp. 156–175.
Cosmetics: Science and Technology (1972), vol. 2, pp. 1–12.
Cosmetics: Science and Technology (1957) pp. 422–437.
Gillette Regular Lather Shave Cream, package label.
Gillette Regular Brushless Shave Cream, package label.
Palmolive Lather Shaving Cream, package label.
Palmolive Brushless Shaving Cream, package label.
Clinique Cream Shave, package label.
The Sharper Image Silicone Formula Shave Gel, package label.
Nivea Rasier Creme, package label.
Perry Ellis Efficient Shave Cream, package label.
Aubrey Organics Herbal Mint & Ginseng Shaving Cream, package label.
Gruene Aloe Cream Shave, package label.
Moore Technique Shaving System, package label.
Shiseido Tactics Shaving Cream, ingredients listing (estimated).

Primary Examiner—Thurman K. Page
Assistant Examiner—James M. Spear
Attorney, Agent, or Firm—Stephan P. Williams

[57] ABSTRACT

The present invention comprises a non-aerosol shaving composition in the form of a clear gel comprising in percent by weight, with the balance being water,
(a) about 15 to 20% of a mixture of potassium myristate and potassium palmitate wherein the myristic acid to palmitic acid ratio is about 2 to 1;
(b) about 2 to 4% Oleth-20;
(c) about 1 to 5% sodium lauroyl sarcosinate; and
(d) about 1 to 2% hydroxyethylcellulose, about 1 to 3% sorbitol, and about 1 to 2% PEG-150 distearate. This composition provides superior shaving attributes compared to other non-aerosol shaving products.

6 Claims, No Drawings

NON-AEROSOL SHAVING GEL

BACKGROUND OF THE INVENTION

This invention relates to a new, non-aerosol shaving gel composition.

Non-aerosol shaving preparations have been available for decades in a variety of forms including bars, sticks, creams and lotions and generally have been of two types—lathering, typically applied with a brush, and non-lathering, typically applied with the fingers. The lathering type is predominantly soap and the non-lathering type is an oil-in-water emulsion.

It is an object of the present invention to provide a non-aerosol shaving composition which is a transparent or clear gel and which provides lather either by application with a brush, sponge or other applicator or by application with the fingers. It is a further object of the present invention to provide a non-aerosol shaving gel composition with advantageous lathering properties, and skin and beard conditioning properties, resulting in superior shave attributes compared to other non-aerosol shaving products.

SUMMARY OF THE INVENTION

The present invention comprises a non-aerosol shaving composition in the form of a clear gel comprising in percent by weight, with the balance being water,
(a) about 15 to 20% of a mixture of potassium myristate and potassium palmitate wherein the myristic acid to palmitic acid ratio is about 2 to 1;
(b) about 2 to 4% Oleth-20;
(c) about 1 to 5% sodium lauroyl sarcosinate; and
(d) about 1 to 2% hydroxyethyl cellulose, about 1 to 3% sorbitol, and about 1 to 2% PEG-150 distearate. In the above formulation, it is preferred to keep the amount of free fatty acid at a level less than about 0.1% in order to maintain clarity at low temperatures.

DETAILED DESCRIPTION OF THE INVENTION

Specific examples of shaving compositions which are embraced by the present inventions and which provide superior shaving attributes have the following formulae, wherein percentages are by weight:

| Ingredient | Ex. 1 | Ex. 2 |
|---|---|---|
| Myristic acid | 10.40 | 9.5 |
| Palmitic acid | 5.15 | 4.7 |
| Potassium hydroxide | 3.66 | 3.3 |
| Oleth-20 | 3.00 | 3.0 |
| Sodium lauroyl sarcosinate | 2.25 | 2.0 |
| Hydroxyethylcellulose | 1.47 | 1.3 |
| Sorbitol | 1.50 | 1.3 |
| PEG-150 distearate | 1.38 | 1.3 |
| Balance water | | |

Optionally, fragrances, dyes and preservatives may be added to the above formulae as deemed necessary or desirable. In addition, about 1.0% aloe vera gel may be added to soothe sensitive skin. It is also advantageous to incorporate in the above formulae about 0.0005 to 0.1% of a fluorosurfactant, such as ZONYL FSK, ZONYL FSA or ZONYL FSN fluorosurfactant, available from DuPont.

It will be readily understood by those skilled in the art that one or more of the components specified in the above formulation may be substituted with equivalent materials. For example, Oleth-20 may be replaced with other known emollients such as Oleth-10 or Laureth-23. Sodium lauroyl sarcosinate may be replaced by the corresponding myristoyl or cocoyl sarcosinates. Sorbitol may be replaced by other known humectants such as glycerin, propylene glycol or Glycereth-26. Hydroxyethylcellulose may be replaced by other known gelling agents such as guar gum, cetyl hydroxyethylcellulose, hydroxypropylcellulose or carbomers. PEG-150 distearate may be replaced by other known thickeners such as PEG-8 distearate or PEG-120 methyl glucose dioleate.

The shaving gel composition of the present invention is made by the following procedure. Hydroxyethylcellulose is dispersed in water in an agitated mixing vessel and heated to about 80°–85° C. When the solution temperature reaches 65° C., the myristic acid, palmitic acid, PEG-150 distearate and Oleth-20 are added. At 80°–85° C., when the fatty acids are melted and homogeneous, aqueous potassium hydroxide is added slowly and the solution is mixed until uniform (about 30–60 min.). The solution is sampled for free fatty acid and adjusted, if necessary, with KOH to bring the free fatty acid level to 0.1% or lower or with myristic/palmitic acid (2:1) if there is free alkali. The solution is cooled to 35° C., with sodium lauroyl sarcosinate (along with optional dyes, perfumes and aloe vera gel) being added at about 45° C., and the product collected as a clear gel.

What is claimed is:

1. A non-aerosol shaving composition in the form of a clear gel consisting essentially of in percent by weight, with the balance being water,
(a) about 15 to 20% of a mixture of potassium myristate and potassium palmitate wherein the myristic acid to palmitic acid ratio is about 2 to 1;
(b) about 2 to 4% Oleth-20;
(c) about 1 to 5% sodium lauroyl sarcosinate; and
(d) about 1 to 2% hydroxyethylcellulose, about 1 to 3% sorbitol, and about 1 to 2% PEG-150 distearate.

2. The non-aerosol shaving composition according to claim 1 wherein the amount of free fatty acid is less than about 0.1%.

3. A non-aerosol shaving composition consisting essentially of about 10.40% myristic acid, about 5.15% palmitic acid, about 3.66% potassium hydroxide, about 3.00% Oleth-20, about 2.25% sodium lauroyl sarcosinate, about 1.50% sorbitol, about 1.47% hydroxyethylcellulose and about 1.38% PEG-150 distearate wherein the amount of free fatty acid is less than 0.1%.

4. The non-aerosol shaving composition according to claim 2 further comprising about 1.0% aloe vera gel.

5. A non-aerosol shaving composition consisting essentially of about 9.5% myristic acid, about 4.7% palmitic acid, about 3.3% potassium hydroxide, about 3.0% Oleth-20, about 2.0% sodium lauroyl sarcosinate, about 1.3% hydroxyethylcellulose, about 1.3% sorbitol and about 1.3% PEG-150 distearate, wherein the amount of free fatty acid is less than 0.1%.

6. The non-aerosol shaving composition according to claim 2 further comprising about 0.0005 to 0.1% of a fluorosurfactant.

* * * * *